United States Patent [19]

Anson et al.

[11] 4,434,800
[45] Mar. 6, 1984

[54] TYMPANOMETRIC APPARATUS

[75] Inventors: Michael Anson, London; Andrew C. Pinder, Barnet; Alan R. Palmer, St. Albans, all of England

[73] Assignee: National Research Development Corporation, London, England

[21] Appl. No.: 385,265

[22] Filed: Jun. 4, 1982

[30] Foreign Application Priority Data

Jun. 10, 1981 [GB] United Kingdom ............... 8117847

[51] Int. Cl.³ ............................................. A61B 6/00
[52] U.S. Cl. ...................................... 128/665; 128/9; 128/746
[58] Field of Search ..................... 128/9, 746, 665; 73/655

[56] References Cited

U.S. PATENT DOCUMENTS 3,596,653  8/1971  Hotchkiss ............................ 128/9
3,952,583  4/1976  Rosati ................................. 73/655
4,339,954  7/1982  Anson et al. ....................... 128/746 X

FOREIGN PATENT DOCUMENTS 2408765  9/1975  Fed. Rep. of Germany ...... 128/746

OTHER PUBLICATIONS

Jako, G. J. et al., "Use of a New Photoelectric Device (Fotonic Sensor) for Vibration Measurements in the Ear," *Journal Acoustical Soc. Am.*, vol. 40, No. 5, p. 1263, Nov. 1966.
Uyemura, T. et al., "Holographic Interferometry for Study on Hearing Mechanism and Combination with Optical Fibers," *Proc. Soc. Photo-Opt. Instrum. Eng.*, (USA), vol. 192, pp. 209–216, (1979).

*Primary Examiner*—Kyle L. Howell
*Assistant Examiner*—Christine A. Fukushima
*Attorney, Agent, or Firm*—Cushman, Darby & Cushman

[57] ABSTRACT

Tympanometric apparatus comprises a housing of two tubular parts (10, 11) interconnected in a T-shape, a first part (10) having an eyepiece (13) and a speculum (12) at its opposite ends, a semi-silvered or dielectric mirror (14) between the ends, and light and sound sources (15, 16) between the mirror and speculum, and the other housing part (11) having a photodetector (19) across a small area thereof and focusing means (22) between this and the first housing part, the light source projecting a beam through the speculum for reflection from a tympanum to be examined, this reflection being partly transmitted through the mirror to the eyepiece and partly reflected again to be focused on the photodetector, and the sound source causing oscillation of the tympanum with consequent variation of the reflection path and photodetector output. Preferably a microphone (23) is also carried by the first housing part to monitor the acoustic pressure adjacent the tympanum. The mirror is suitably of dichroic form and preferably transmits visible light while reflecting infrared.

10 Claims, 1 Drawing Figure

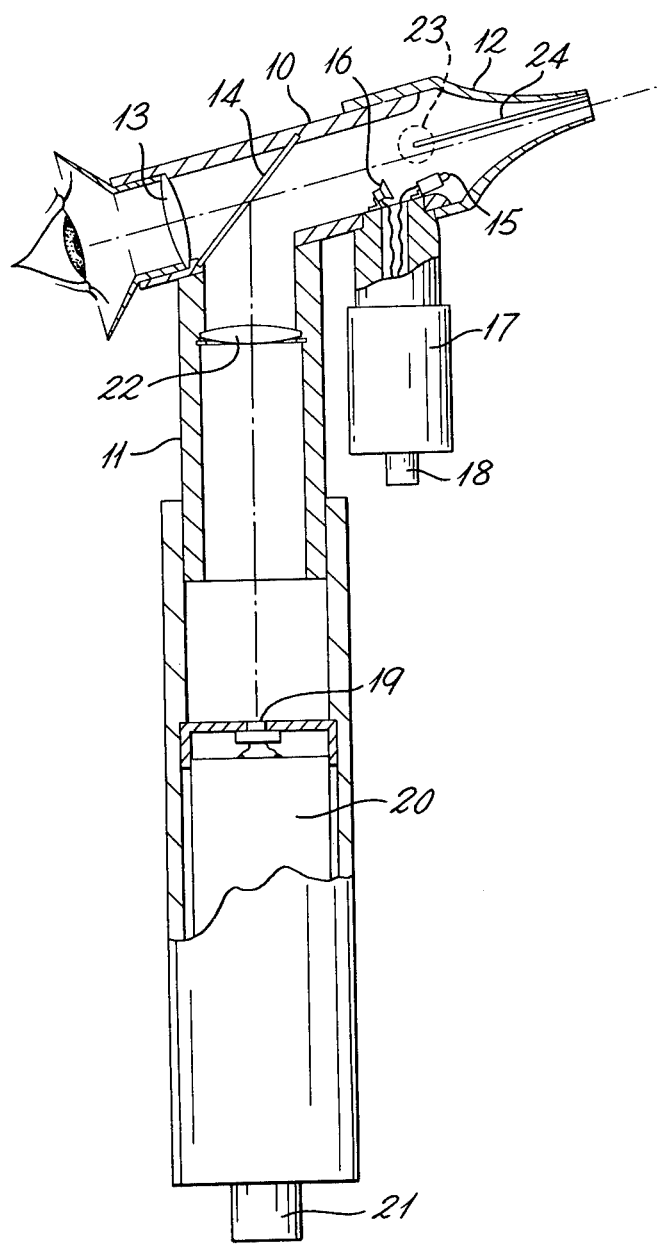

TYMPANOMETRIC APPARATUS

In UK patent application No. 8010380 published on Dec. 3, 1980 under No. 2,047,894A and which corresponds to Anson et al U.S. Pat. No. 4,339,954 issued July 20, 1982, there is described a basis for tympanometric apparatus involving the generation and analysis of speckle and interference patterns resulting from illumination of the tympanum, during oscillation by sound stimulation, with coherent light. Although the development of a clinical apparatus of this form appears quite practicable, it is evident that such an apparatus will be relatively complex and costly compared to conventional otological equipment and therefore likely to be confined to limited usage, typically in specialist institutions.

It has accordingly been thought desirable to pursue the possibility of developing a simpler and less costly apparatus capable of a similar function in wider clinical usage. To this end experiments were conducted with modifications of the original form of apparatus employing incoherent light, but initially no output signals of value were detectable. However, continued development has changed this situation and a further, simpler form of apparatus appears to be practicable.

Accordingly the present invention provides tympanometric apparatus comprising a housing including first and second mutually transversely communicated portions of generally tubular form, said first housing portion having a speculum at one end thereof, viewing means at the other end thereof, first optical means located between said speculum and viewing means, and a light source and sound source both located between said speculum and first optical means and respectively operable to project a light beam and sound through said speculum, and said second housing portion communicating with said first housing portion adjacent to said first optical means, having a photodetector extending across a small area thereof spaced from said first optical means, and second optical means located between said photodetector and said first optical means, said speculum affording application of said beam and sound towards the tympanum of a subject to be examined with the apparatus, said first optical means partially transmitting and reflecting reflection of said beam from said tympanum respectively towards said viewing means and photodetector, said viewing means facilitating direction of said speculum relative to said tympanum, said second optical means focusing said beam reflection in the plane of said photodetector, and said sound causing oscillation of said tympanum with consequent variation in the optical path of said reflection and the output of said photodetector.

It is to be understood that the term "light" in the present context is intended, unless otherwise qualified, to embrace visible light and bordering parts of the electromagnetic spectrum, particularly infrared, sometimes referred to as non-visible or near-visible light.

A fuller understanding of the invention will be gained from the following more detailed description of one embodiment thereof with reference to the accompanying drawing which diagrammatically illustrates the embodiment.

The drawing in fact shows a hand-held instrument which has been produced by modification of a conventional otoscope which served to provide the principal parts of the housing and some of the components therein.

The housing, as indicated above, includes two mutually transversely communicated parts of generally tubular form. These parts comprise a crossbar part 10 and stem part 11 forming a generally T-shaped configuration, with the latter part being hand-held during use. The part 10 terminates at one end in a speculum 12 and at its other end forms an eyepiece 13 as denoted by the provision of flaring to form a monocular shield around a lens.

A semi-silvered or dielectric mirror 14 is located across the housing part 10 adjacent to its junction with part 11, this mirror serving to transmit to the eyepiece light entering the instrument through the speculum, and also to reflect such light into the part 11. The light in question will itself be reflection from a tympanum towards which the speculum is directed, this light originating from a source in the form of a miniature bulb 15 of which the envelope incorporates a lens. This bulb is located in the housing part 10, to one side thereof and between the speculum and mirror, to project a beam through the speculum.

A sound source in the form of a miniature loudspeaker 16 is similarly located in the housing part 10 to project sound through the speculum.

The location of the bulb and loudspeaker in the housing part 10 is conveniently effected by mounting these components on one end of an additional housing part 17 connected into the side of part 10 and projecting therefrom alongside the other housing part 11. This projection additionally serves to carry terminals 18 for the connection of appropriate electrical supplies to the bulb and loudspeaker.

The housing part 11 carries, in sequence towards its free end, a photodetector in the form of a silicon photodiode 19 extending across a small central area within the part 11, a preamplifier 20 for the photodiode output, and terminals 21 for connecting the amplified output to analysis means described below. Additionally, the part 11 houses optical components denoted as a lens 22 for focusing reflected light from the mirror 14 in the plane of the photodiode 19.

Use and operation of this instrument is largely self-evident from the foregoing description. The instrument is held by the housing part 11 and the speculum directed, by way of the external ear canal, towards a tympanum to be examined. The tympanum is illuminated by energization of the bulb, and direction of the speculum is facilitated by viewing through the eyepiece to which light reflected from within the ear is transmitted by the mirror. At the same time this light is reflected by the mirror to be focused in the plane of the photodiode. Energisation of the loudspeaker projects sound into the ear to oscillate the tympanum and this oscillation will produce a corresponding variation in the reflection path and, as a result, a representative variation in the photodiode output. The principal factor in this variation is, then, the change in brightness of the illuminated area of the tympanum, as viewed by the photodiode, due to the change in angle of orientation of the area of illumination relative to the source and photodiode directions caused by the motion of the tympanum. As it is change of angle of the illuminated part of the tympanum which produces the signal variation of interest, the magnitude of this variation is dependent on the spacial derivative of the amplitude of the oscillation of that part.

In practice the signal variation of interest will be small due to the inherent problems of the associated anatomical geometry and the reflective properties of the tympanum. However, the variation is very stable in both amplitude and phase, and this enables the use of signal averaging techniques to be used to good effect for the analysis of transient response to impulse sound stimulation which, in turn, is useful in facilitating the generation of a frequency response characteristic for the ear under examination. In the case of continuous wave sound stimulation for the analysis of function related to specific frequencies, phase sensitive detection can be employed.

In initial testing of the invention the output signal variations of interest have been found to be convoluted with artifactual resonances produced by the acoustic properties of the instrument itself. These resonances may be eliminated by appropriate design of the instrument, but alternative possibilities can be adopted. One possibility is to monitor the acoustic pressure close to the tympanum with a miniature microphone and then to deconvolute the signals by the microphone response using a computer. This last course has in fact been adopted for a current trial with an instrument as illustrated by the location of a miniature microphone 23 on the outside of the housing part 10, this microphone detecting the acoustic pressure by way of a tube 24 passing into the housing and towards the speculum, and having its output applied to terminals 18. Another possibility is to provide a predistortion of the stimulating sound field by an appropriate computer generation to reduce errors to an acceptable level.

While the invention has been described in more detail with reference to the illustrated embodiment, it is not intended to be limited thereby but is capable of variation.

For example reference has been made to the possibility of monitoring sound pressure in relation to deconvolution of the output signals and the associated microphone may be located in the instrument itself for this purpose, the sound stimulus may be applied to the instrument by way of a tube, and a tube connection may also be employed to allow positive or negative pressurisation of the ear canal. This last, and other operations with the instrument, will require the use of an ear seal.

Variation is also possible in the choice of optical components. The instrument presently under trial employs a dielectric mirror of dichroic form to transmit visible light and reflect infrared, but a semi-silvered mirror can be used as an alternative and the mirror can be dichroic or not whether dielectric or semi-silvered. The photodiode is, of course, selected for sensitivity to the reflected light incident thereon.

The light source may be coloured, and may be in the form of a semi-conductor laser or light emitting diode rather than the presently employed filament bulb.

Also fiber optic guides may be employed to conduct light from the source, or the tympanic reflection thereof, through the speculum.

Lastly, light from an auxiliary source may be employed to project a spot, graticule, or other formation through the speculum to facilitate targeting of the instrument.

We claim:

1. Tympanometric apparatus comprising a housing including first and second mutually transversely communicated portions of generally tubular form, said first housing portion having a speculum at one end thereof, viewing means at the other end thereof, first optical means located between said speculum and viewing means, and a light source and a sound source both located between said speculum and first optical means and respectively operable to project a light beam and sound through said speculum, and said second housing portion communicating with said first housing portion adjacent to said first optical means, having a photodetector extending across a small area thereof spaced from said first optical means, and second optical means located between said photodetector and said first optical means, said speculum affording application of said beam and sound towards the tympanum of a subject to be examined with the apparatus, said first optical means partially transmitting and reflecting reflection of said beam from said tympanum respectively towards said viewing means and photodetector, said viewing means facilitating direction of said speculum relative to said tympanum, said second optical means focusing said beam of reflection in the plane of said photodetector, and said sound causing oscillation of said tympanum with consequent variation in the optical path of said reflection and the output of said photodetector.

2. Apparatus according to claim 1 wherein said light source is a filament bulb.

3. Apparatus according to claim 1 wherein said first optical means is a semi-silvered mirror.

4. Apparatus according to claim 1 wherein said first optical means is a dielectric mirror.

5. Apparatus according to claim 1 wherein said first optical means is of dichroic form.

6. Apparatus according to claim 5 wherein said mirror transmits visible light and reflects infrared.

7. Apparatus according to claim 1 wherein said photodetector is a photodiode.

8. Apparatus according to claim 1 wherein said sound source is a miniature loudspeaker.

9. Apparatus according to claim 1 wherein said second housing portion carries therein a preamplifier operably coupled with said photodetector.

10. Apparatus according to claim 1 wherein said first housing portion carries a miniature microphone to detect the acoustic pressure adjacent said tympanum.

* * * * *